(12) United States Patent
Thomke et al.

(10) Patent No.: US 8,444,643 B2
(45) Date of Patent: May 21, 2013

(54) CLAMPING ELEMENT AND INSERT THEREFOR

(75) Inventors: Roland Thomke, Bellach (CH); Damian Fankhauser, Bern (CH)

(73) Assignee: Stryker Trauma SA (CH)

( * ) Notice: Subject to any disclaimer, the term of this patent is extended or adjusted under 35 U.S.C. 154(b) by 347 days.

(21) Appl. No.: 12/227,836

(22) PCT Filed: May 29, 2007

(86) PCT No.: PCT/CH2007/000270
§ 371 (c)(1),
(2), (4) Date: Apr. 15, 2009

(87) PCT Pub. No.: WO2007/137443
PCT Pub. Date: Dec. 6, 2007

(65) Prior Publication Data
US 2009/0306661 A1  Dec. 10, 2009

(30) Foreign Application Priority Data
May 29, 2006 (EP) .................................. 06114661

(51) Int. Cl.
*A61B 17/70* (2006.01)
(52) U.S. Cl.
USPC .............................. 606/54; 606/278; 606/253
(58) Field of Classification Search
USPC . 606/60, 74, 246–279, 324; 623/17.11–17.16
See application file for complete search history.

(56) References Cited

U.S. PATENT DOCUMENTS

| 4,621,627 | A | * | 11/1986 | DeBastiani et al. | 606/57 |
| 4,821,382 | A | * | 4/1989 | Puschkarski | 24/298 |
| 5,281,222 | A | * | 1/1994 | Allard et al. | 606/54 |
| 5,312,405 | A | * | 5/1994 | Korotko et al. | 606/278 |
| 5,476,462 | A | * | 12/1995 | Allard et al. | 606/60 |
| 5,501,684 | A | * | 3/1996 | Schlapfer et al. | 606/301 |
| 5,507,746 | A | * | 4/1996 | Lin | 606/264 |
| 5,601,551 | A | * | 2/1997 | Taylor et al. | 606/54 |
| 5,662,650 | A | * | 9/1997 | Bailey et al. | 606/59 |
| 5,752,954 | A |   | 5/1998 | Mata et al. |  |
| 5,788,695 | A | * | 8/1998 | Richardson | 606/57 |
| 5,891,144 | A | * | 4/1999 | Mata et al. | 606/59 |
| 6,024,745 | A | * | 2/2000 | Faccioli et al. | 606/54 |
| 6,036,691 | A | * | 3/2000 | Richardson | 606/57 |
| 6,342,054 | B1 | * | 1/2002 | Mata | 606/59 |

(Continued)

FOREIGN PATENT DOCUMENTS

| EP | 0 577 219 B1 | 1/1994 |
| EP | 0 700 664 B1 | 9/1999 |

(Continued)

*Primary Examiner* — Ellen C Hammond
*Assistant Examiner* — Stuart S Bray
(74) *Attorney, Agent, or Firm* — Lerner, David, Littenberg, Krumholz & Mentlik, LLP

(57) ABSTRACT

An insert (70) for a clamping element with two jaws to clamp a rod-shaped element comprises an inner cavity (144) to accommodate a rod-shaped element and at least one flange element (153) at one longitudinal end of the insert intended to abut against the clamping element. The flange element (153) comprises clamping members (161) to reduce the available room within the inner cavity (144) for the rod-shaped element to be clamped and to clamp the flange element (153) between the rod-shaped element and an outer clamping surface of the clamping element to prohibit any longitudinal movement of the clamped insert.

10 Claims, 5 Drawing Sheets

U.S. PATENT DOCUMENTS

| | | | |
|---|---|---|---|
| 6,423,061 B1 * | 7/2002 | Bryant | 606/57 |
| 6,565,564 B2 * | 5/2003 | Hoffman et al. | 606/59 |
| 6,616,664 B2 | 9/2003 | Walulik et al. | |
| 7,618,417 B2 * | 11/2009 | Thomke et al. | 606/59 |
| 7,819,902 B2 * | 10/2010 | Abdelgany et al. | 606/267 |
| 8,206,388 B2 * | 6/2012 | Thomke et al. | 606/59 |
| 2002/0142674 A1 * | 10/2002 | Chadbourne et al. | 439/783 |
| 2003/0191467 A1 * | 10/2003 | Hoffmann-Clair et al. | 606/59 |
| 2006/0052781 A1 * | 3/2006 | Thomke et al. | 606/59 |
| 2006/0167453 A1 * | 7/2006 | Hoffmann-Clair et al. | 606/59 |
| 2006/0212036 A1 * | 9/2006 | Bianchi et al. | 606/72 |
| 2007/0016188 A1 * | 1/2007 | Boehm et al. | 606/60 |

FOREIGN PATENT DOCUMENTS

| | | |
|---|---|---|
| EP | 1 184 000 A1 | 3/2002 |
| EP | 1 627 608 A1 | 2/2006 |
| FR | 2 743 290 A1 * | 7/1997 |
| FR | 2 806 615 A | 9/2001 |
| FR | 2 806 615 A1 * | 9/2001 |
| GB | 1 209 021 A | 10/1970 |

* cited by examiner

US 8,444,643 B2

CLAMPING ELEMENT AND INSERT THEREFOR

TECHNICAL FIELD OF THE INVENTION

The invention pertains to a clamping element for the clamping of a rod-shaped element of an articulation element, particularly a clamping element of an articulation element for the stabilization of bone fractures. The invention also pertains to an insert for such a clamping element adapting such clamping element for rod-shaped elements of a smaller diameter.

TECHNICAL BACKGROUND OF THE INVENTION

EP 1 184 000 describes a single-piece clamping element with two opposing cavities and one laterally open cavity to receive a clamping jaw forming a rod-shaped element and a hinge, which is arranged opposite the cavity, connecting the clamping jaws so that they are movable on top of each other, with each clamping jaw having one bore each aligned flush with one another.

This clamping element has the advantage that an articulation can be produced with two identical clamping elements arranged next to one another, inserting a connecting screw through the bore, which is screwed into an internally threaded nut to close the clamping jaws.

From EP-A-0 700 664 an articulation is known consisting of two times two individual clamping jaw elements and one central screw. This articulation allows the lateral insertion of one or two rod-shaped elements into the corresponding cavities. U.S. Pat. No. 5,752,954 has a spring arranged between the two center clamping jaw elements, which spring tension allows the clipping in of the rod-shaped elements and holding the jaw elements on the rod-shaped elements before the articulation element is blocked. U.S. Pat. No. 6,616,664 provides for narrow lateral lever arms to hold laterally inserted rod-shaped elements before the articulation is blocked. U.S. Pat. No. 6,342,054 has an external spring.

Based on this state of technology, it is one role of the invention at hand to indicate a single-piece or two-piece clamping element which allows the longitudinal insertion of a rod-shaped element and which, when utilized dually, is directly applicable as an articulation element. It is another object of the invention to obtain a single-piece clamping element with advantages being usable for rod-shaped elements with different diameters.

Another goal of the invention is the creation of a cost-effective disposable clamping element, particularly made of, a synthetic material (such as plastic) injection molding, which does not have the structural disadvantages of X-ray transparent clamping elements as in EP 1 184 000. Especially it is an object of the invention to realize a disposable clamping element being able to support and transmit large pressure forces for rod-shaped elements with different diameters.

Based on the known state of technology, another, role of the invention is also to provide an improved articulation element.

SUMMARY OF THE INVENTION

An insert for a clamping element with two jaws to clamp a rod-shaped element is provided with an inner cavity to accommodate a rod-shaped element and at least one flange element at one longitudinal end of the insert intended to abut against a clamping element. Then the flange element comprises clamping members to reduce the available room within the inner cavity for the rod-shaped element to be clamped and to clamp the flange element between the rod-shaped element and an outer clamping surface of the clamping element to prohibit any longitudinal movement of the clamped insert. Such a combination of features allow the simple use of plastic material for the clamping element as well as for the insert itself without reducing the possible clamping force.

The clamping members can be slits provided within the insert itself or free ends of the flanges, which are clamped by corresponding outer surfaces of the jaws, to create an identity of clamped items, i.e. the rod at the innermost place, the surrounding insert and the encompassing clamping element with its jaws.

BRIEF DESCRIPTION OF THE FIGURES

Now the invention is more closely described with reference to the drawings and with the aid of a number of embodiments.

DETAILED DESCRIPTION OF PREFERRED EMBODIMENTS

Figure 1:
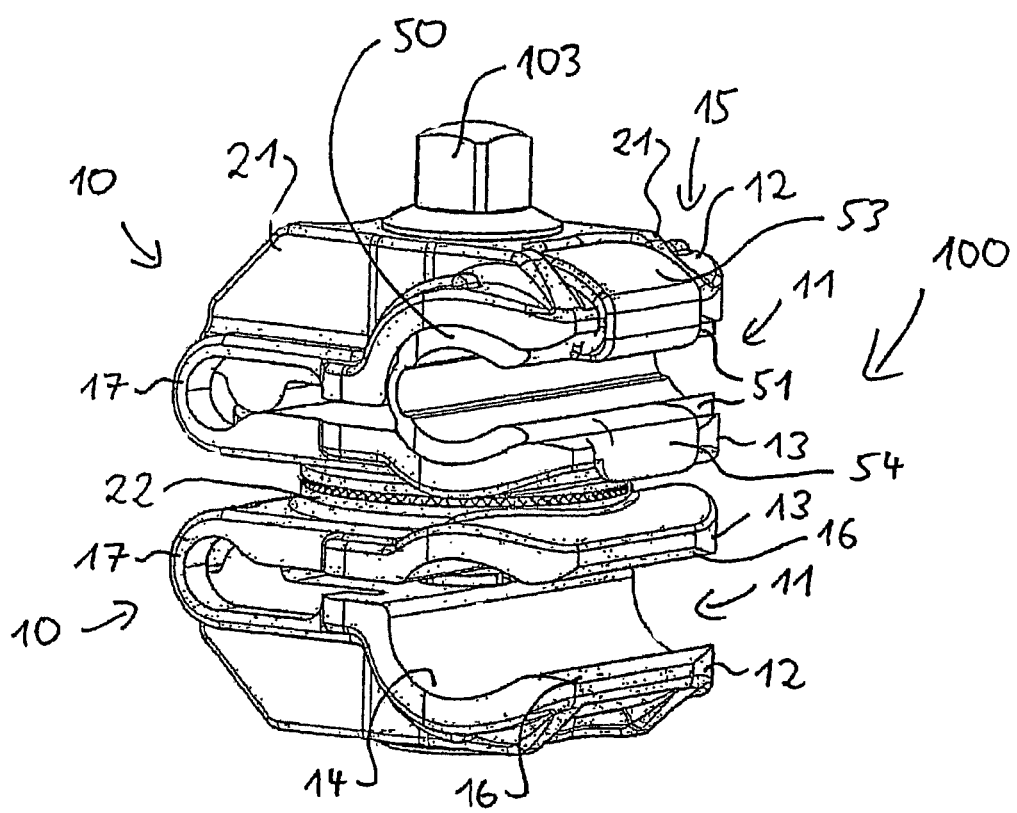
FIG. 1 shows a perspective view of an articulation element with two clamping elements and an insert according to prior art.
Figure 2:
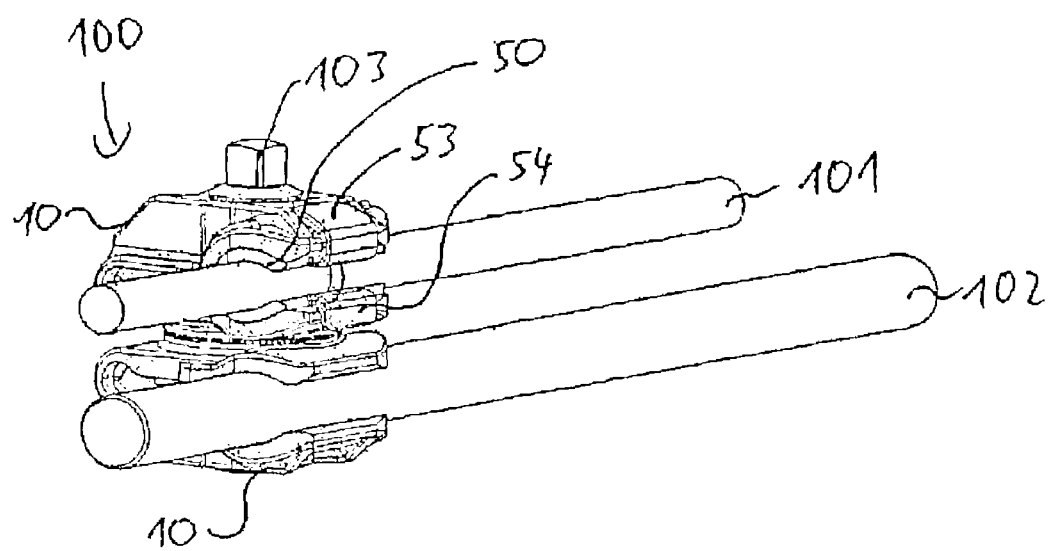
FIG. 2 shows a perspective view of the articulation element of FIG. 1 with two rod-shaped elements.

FIGS. 1 and 2 shows a perspective view of an articulation element 100 with two clamping elements 10. The clamping element 10 has two clamping jaws 12 and 13 creating together one cavity 11 to receive a rod-shaped element. The cavity 11 is formed by transversely running grooves 14. The outer edges 16 of the side facing clamping jaws 12 and 13 are slanted to simplify the lateral insertion of a rod-shaped element. Across from the cavity 11 and the slanted outer edges 16, a pivotal bearing 17 is arranged.

When the clamping element 10 is intended for a rod with 4 to 6 millimeters in diameter, the opening at the free ends has a diameter of, for instance, 2 millimeters in a resting position. If the clamping element 10 is intended for a rod with a diameter of 12 millimeters, the opening at the free ends has a diameter of, for instance, 9 millimeters in a resting position.

In the upper area of the clamping jaw 12 the area between cross ribs 21 has been excluded with the exception of a round screw receptacle. Only the screw head 103 can be seen. Screw receptacle, for instance, has a conical shoulder area or a step shoulder, which merges into a continuous bore in the top clamping jaw 12.

In the lower clamping jaw 13 cross ribs 21 end in a ring flange 22, which, for instance, may have a flat recessed ring shaped step, where a weight and material saving recess advantageous for injection molding can be connected, with a bore in the center.

This continuous bore is aligned flush with the abovementioned bore in top clamping jaw 12. At the clamping element 10, it runs vertically to the axis of the cavity 11. The bore is cylindrical and in its interior, it may have guide ribs arranged in regular intervals, preferably between three or five ribs.

One clamping element 10 with the jaw parts 12 and 13 comprises semi-cylindrical portions running over the whole width of the jaw 12 and being directed to a complementary groove in jaw 13. The stops may be chosen shorter or in smaller portions with intermediate regions. The stops are running parallel to the cavity 11.

An insert 50 is lodged within the cavity 11, comprising cylindrical wall portions 51 defining inner and outer curved surfaces, wherein the wall portions 51 are connected by a web. The web is thinner than the wall portions 51. The outer surfaces of the insert 50 are complementary to the surfaces of the grooves 14. The insert 50 according to FIG. 1 comprises two holding extensions 53 and 54, extending away from the inner room of the insert 50 and engaging a respective corresponding surface between the ribs 21. These corresponding surfaces of the insert 50 avoid lateral displacement of the insert 50 in the direction of a rod to be introduced. The holding extensions 53 and 54 also avoid the rotation of the insert itself.

FIG. 2 shows the use of an articulation element 100 according to FIG. 1 as an articulation element with two clamping elements 10 and one insert 50. All identical or similar features have received the same reference numerals. The rod-shaped element 102 having a greater diameter is directly clamped between the jaws 12 and 13. The smaller diameter rod-shaped element 101 is not directly clamped between the jaws 12 and 13 but between the corresponding surfaces of the insert 50.

FIG. 1 and FIG. 2 show the principles of clamping rod-shaped elements. The following description discloses new clamping elements and especially inserts, which can be used with modified clamping elements according to FIG. 1 as explained later.

Figure 3:
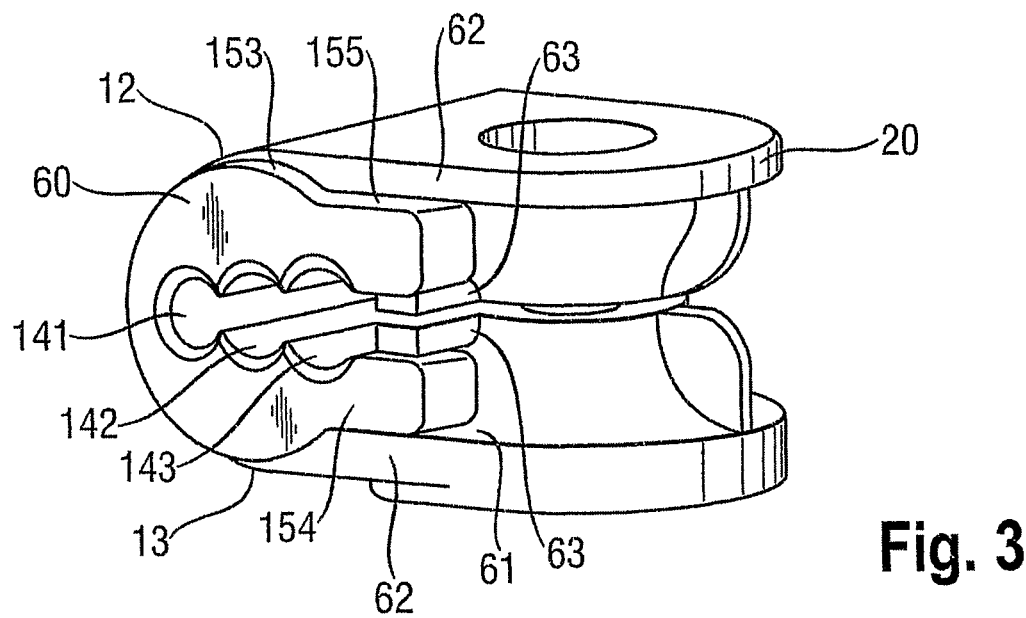
FIG. 3 shows a perspective view of a clamping element according to a first embodiment of the invention and an insert according to a first embodiment of the invention.
Figure 5:
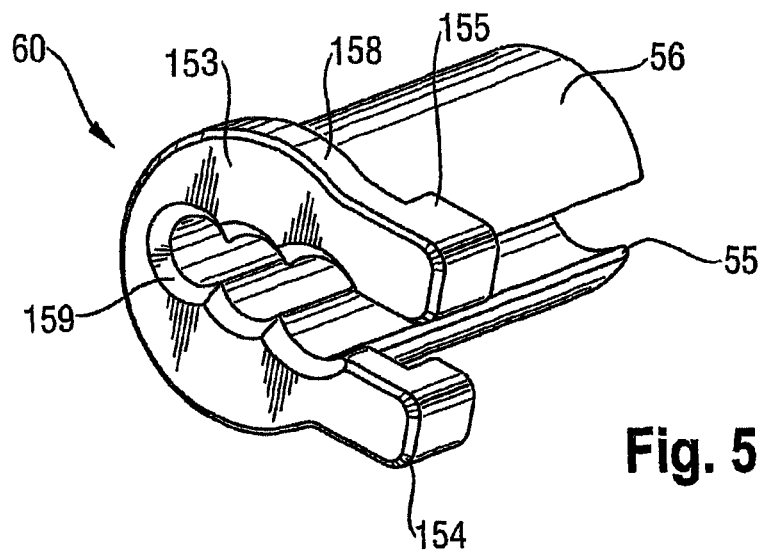
FIG. 5 shows a perspective view of the insert according to FIG. 3.
Figure 6:
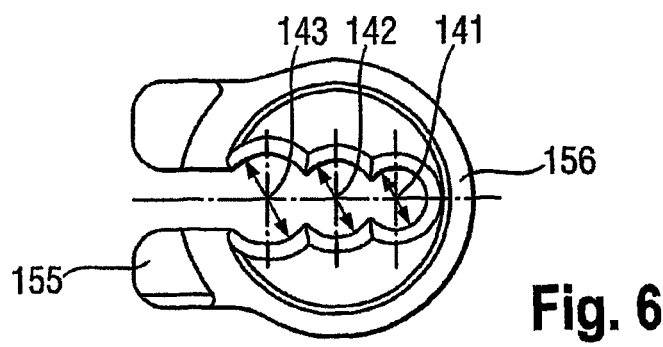
FIG. 6 shows a front view of the insert according to FIG. 5.
Figure 7:
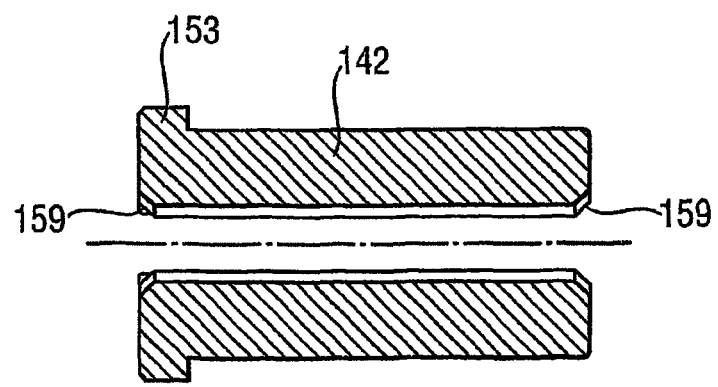
FIG. 7 shows a sectioned lateral view of the insert according to FIG. 5.

FIG. 3 now shows a single-piece clamping element 20 according to a first embodiment of the invention, having received a single-piece insert 60. The single-piece insert 60 is shown in three detailed views in FIGS. 5, 6 and 7, comprising three reception grooves 141, 142 and 143, extending in the longitudinal direction of the insert 60. The reception grooves 141, 142 and 143 show, in a cross-sectional view, parts of circles with a radius of 4, 5 or 6 millimeter, wherein the centers are placed on the axis of insert 60. Instead of a holding extension 53 there is a flange 153, having the shape of a C. The flange 153 has free ends 154, engaging complementary recesses 61 within the clamping element 60. The free ends 154 each comprise a nose 155, engaging the recess 61 and forming a gripping element. The connecting portion 156 opposite to the free ends can be thinner or omitted in other embodiments, to improve the flexible movement of the web. The orifices of the grooves 141, 142 and 143 comprise chamfers 159 to enable a smoother longitudinal introduction of rods, preferably at both ends of the insert 60.

The sequence of grooves 141, 142, 143 defines apertures for rods of different diameters. The distance of the central points of the grooves 141, 142, 143 is smaller then the diameter of the corresponding rods. The centered groove 142 is oriented concentrically to the outer surface 56 of the insert 60. The distance between the center of this groove 142 to the center of the smallest groove 141 is smaller than the distance to the center of the larger groove 143.

The clamping element 20 of the embodiment of FIG. 3 is a single-piece clamping element encompassing the insert 60. The free ends 154 are located between the upper outer rims 62 of the jaws 12 and 13 and inner noses 63 of the jaws. These noses 63 and the rims 62 form the above-mentioned recesses 61 to accommodate one free end 154, respectively. The longitudinally oriented surface of each recess 61 provides an abutting surface for the insert 60. It is also possible to provide larger free ends 154 encompassing the function of the noses 63, wherein, when the flange 153 is clamped, the inner parts of the free ends 154 are pressed one against another.

Therefore the jaws 12 and 13 are pushing the free ends 154 one towards the other and, since they are provided within the recesses 61, the inner noses 63 are moved one towards the other. Therefore the clamping force finally fixes the free ends 153 in the recesses 61 between the outer rims 62 and ensures that the insert 60 cannot be displaced in a longitudinal direction and therefore improves the holding properties, since the flanges 153 themselves are clamped by the jaws 12, 13.

It is noted that within another embodiment not shown in the FIG. the insert 60 can also be turned by around 180 degree, wherein the noses 163 of the modified clamping element are then provided on the free ends of the jaws 12 and 13. Then jaws 12, 13 and free ends 154 are oriented in the same direction allowing for a lateral introduction of a rod over the edge 55 of insert 60. The web 156 is then thinner and can preferably by bent to allow a better closing of the jaws. Such an insert 60 would then be preferably used with a two-piece clamping element or with a clamping element similar to the clamping element of FIG. 1 with noses 63 near the longitudinal ends of edges 16. Although it is possible and preferred to use only one flange 153 it is possible that the insert 60 has two flanges 153 at opposite longitudinal ends.

Figure 4:
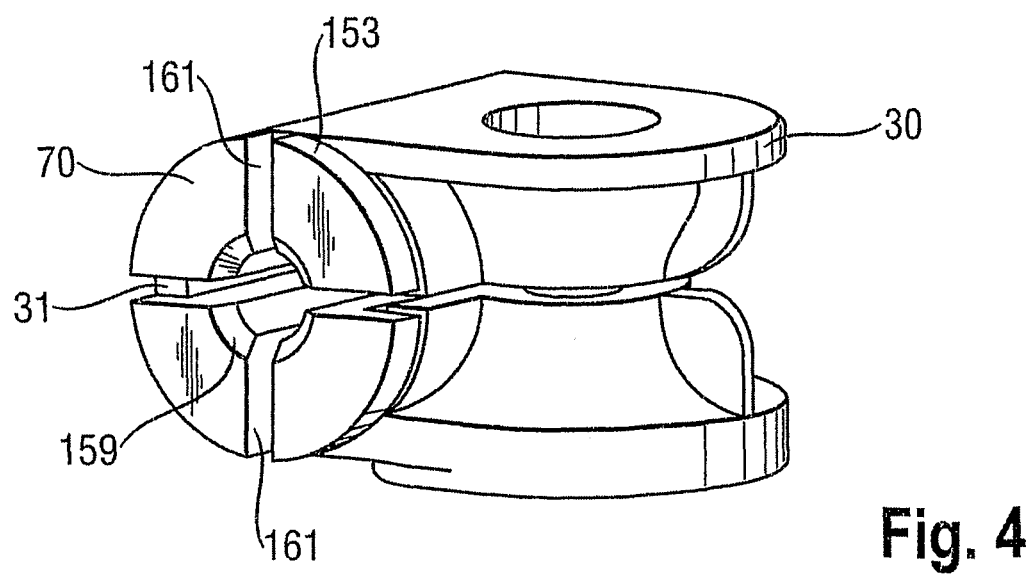
FIG. 4 shows a perspective view of a clamping element according to a second embodiment of the invention and an insert according to a second embodiment of the invention.
Figure 8:
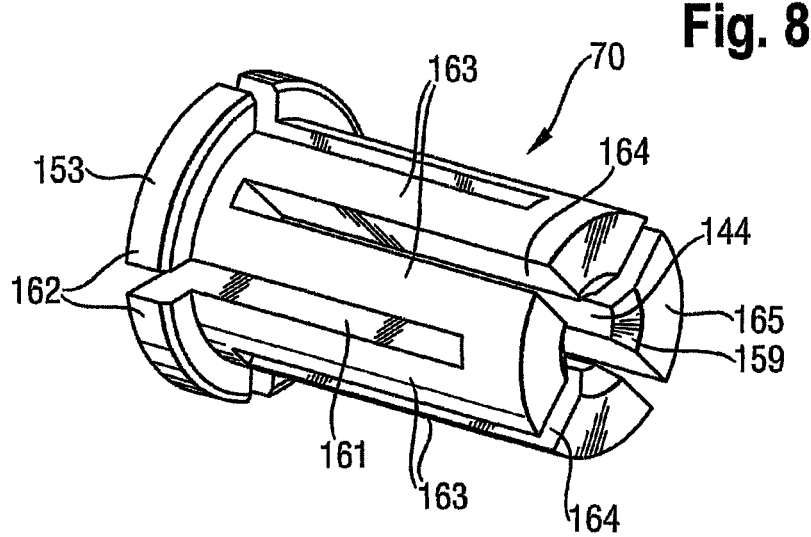
FIG. 8 shows a perspective view of the insert according to FIG. 4.
Figure 9:
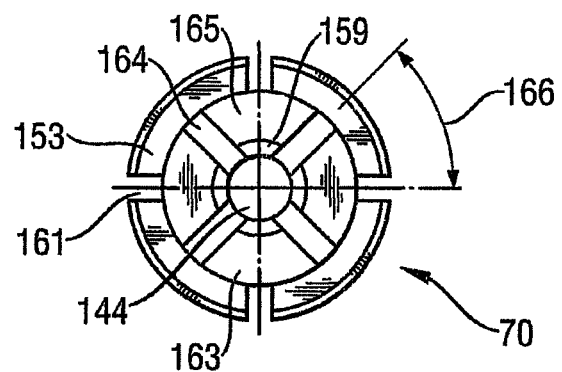
FIG. 9 shows a front view of the insert according to FIG. 4.
Figure 10:
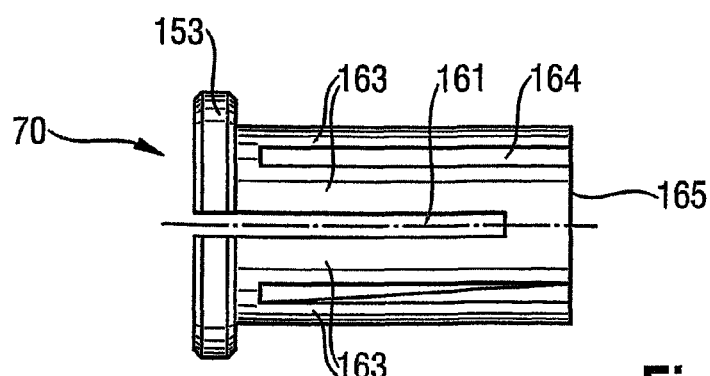
FIG. 10 shows a sectioned lateral view of the insert according to FIG. 4.

FIG. 4 shows a perspective view of a clamping element 30 according to a second embodiment of the invention and an insert 70 according to a second embodiment of the invention. Clamping element 30 is a single-piece clamping element 30 encompassing the insert 70 with a semicircular shell surface 31. Insert 70 comprises a flange 153 divided into four segments 162 with separating slits 161. Each flange segment 162 continues in the insert 70 as a hollow cylindrical portion 163. Each hollow cylindrical portion 163 is separated from its neighbour portion 163 by a slit 161. Each hollow cylindrical portion 163 is furthermore separated into a fork-like form through further slits 164 running from the opposite side of the insert. As can be seen from FIG. 8 these slits 161 and 164 are creating a meander form for the insert 70, defined between the flange 153 and the bottom surfaces 165. Preferably, the slits 161 and 164 have the same width over the longitudinal length and the radial depth, they have parallel sides (and not radially tapering sides), the lengths are such that the remaining longitudinal portion is identical near surface 165 and flange 153, and the angle 166 between two neighbouring slits 161 and 164 is 45 degrees.

At both ends there are chamfered surfaces 159 to facilitate introduction of rods. The diameter of the rods to be used depends on the inner hollow diameter 144 of the insert 70. It is clear that different rods can be clamped since the eight segments 163 spanning around a rod at any cross-section in the middle of the insert and the four segments at the free ends of the insert 70 allow for a compression of the corresponding slits 161 and/or 164. At the same occasion, the insert 70 is clamped between the jaws 12 and 13 ensuring the stop of any lateral displacement of the insert in relation to the clamping element.

It is emphasized that the term embodiment in the previously mentioned description does not mean that only the elements described with respect to the respective clamping element or articulation element are subject of the invention. In particular, these are also combinations of the characteristics described in objects of various embodiments and FIGS. For instance, a modified clamping element is an object of the invention, which has a groove 14 per FIG. 1 and accepts an insert 50 per FIG. 4, thus comprising noses 63 as shown within the embodiment of FIG. 3.

Although the simplicity of the construction enables the use of low-cost plastic material for the clamping element as well as for the insert, it is also contemplated to use plastic inserts within metallic clamping elements.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A clamping assembly for clamping an elongate rod comprising:
    a clamping element having opposing first and second moveable clamping jaws, each clamping jaw having an outer rim and inner nose defining a longitudinal recess therebetween extending along a longitudinal axis, wherein the first and second clamping jaws are hingedly connected such that the inner nose of the first clamping jaw is adjacent to the inner nose of the second clamping jaw;
    a clamp insert mounted in the clamping element longitudinal recess having a hollow body comprising a first and second longitudinal end, an inner cavity defined therein extending from the first longitudinal end through the second longitudinal end for accommodating the elongate rod, a space running from the first longitudinal end through the second longitudinal end of the hollow body thereby forming at least two insert jaws for clamping the elongate rod, the insert jaws having spaced free ends, the inner cavity having three reception grooves offset from one another in a direction transverse to the longitudinal axis, a cross-sectional area of each groove decreasing on moving inwardly from the spaced free ends;
    the first longitudinal end of the clamp insert comprises a flange, the flange comprises a first and second free end, wherein each of the free ends comprise a nose for slidable insertion into the corresponding recess of each of the clamping jaws and for slidably engaging the inner nose and outer rim of the corresponding clamping jaw, thereby prohibiting the longitudinal and rotational movement of the clamp insert with respect to the longitudinal axis of the clamping element.

2. The clamping assembly of claim 1, wherein the inner cavity is comprised of at least three reception grooves of differing cross sectional areas, wherein each reception groove has a central axis that is parallel and coplanar with the central axes of the remaining reception grooves.

3. The clamp assembly of claim 1, wherein the at least three reception grooves of the clamp insert are cylindrical.

4. A clamp insert for a clamping assembly for clamping an elongate rod comprising:
    a body having a first and second longitudinal end, at least three reception grooves of differing cross sectional area defining an inner cavity therein extending from the first longitudinal end through the second longitudinal end for accommodating the elongate rod each groove having a longitudinal centerline, an opening running from the first longitudinal end through the second longitudinal end of the body extending through the centerline of the at least three reception grooves thereby forming at least two moveable insert jaws for clamping the elongate rod,
    the movable insert jaws each having a free end defining a space therebetween,
    the three reception grooves longitudinal centerlines offset from one another in a direction transverse to the longitudinal direction, a cross-sectional area of each groove decreasing in size on moving inwardly from the free ends of the moveable insert jaws,
    the first longitudinal end comprises a flange for prevention of longitudinal translation with respect to a clamping element,
    each of the at least three reception grooves central axis is parallel and coplanar with the central axes of the remaining reception grooves.

5. The clamp insert of claim 4, wherein the flange further comprises a first and second free end, wherein each of the free ends further comprise a nose for slidable insertion into a recess of a clamping element, thereby prohibiting the longitudinal and rotational movement of the clamp insert with respect to the clamping element.

6. The clamp insert of claim 4, wherein the at least three reception grooves are cylindrically shaped.

7. An articulation element having first and second clamping elements, at least one of the two clamping elements comprising:
    two opposing moveable first and second clamping jaws, each having a bore aligned with one another and having free ends for receiving a rod-shaped element,
    an insert having a cylindrical body including a center longitudinal axis,
    the first and second clamping jaws forming an inner cavity to receive the rod-shaped element or said insert,
    wherein the insert body comprises a first and a second longitudinal end, the first longitudinal end comprising a flange element and the insert body defines an inner cavity to accommodate a rod-shaped element,
    the flange element comprising clamping members to reduce the available space within the insert inner cavity for the rod-shaped element to be clamped and to clamp the flange element between the rod-shaped element and an outer clamping surface of the clamping element to prohibit any longitudinal movement of the clamped insert, the insert body inner cavity having first, second and third grooves extending longitudinally from the insert first end to the insert second end, the first, second and third grooves having longitudinally extending center lines offset from one another in a direction transverse to the longitudinal direction, the first, second and third grooves having different size cross-sections, the cross-sections decreasing in size inwardly from the first and second clamping jaw free ends, each groove having a longitudinal opening extending from the insert first longitudinal end to the second longitudinal end, the opening extending parallel and coplanar with the center lines of the first, second and third grooves,
    wherein the flange element at the first longitudinal end of the insert has spaced free ends adjacent the largest groove and a nose extending in a radial direction to the cylindrical body longitudinal axis, the nose is adapted to abut against an abutting surface of the clamping element to prevent rotation of the cylindrical body about the longitudinal axis thereof.

8. The clamping element according to claim 7, wherein the first and second clamping jaws have inner noses to provide a second additional inner abutment surface for the free ends of the flange element.

9. A clamp insert for a clamping assembly for clamping an elongate rod comprising:

two opposing moveable first and second clamping jaws, each having a bore aligned with one another, the first and second jaws defining a recess therebetween, an insert having a body with a first and second longitudinal end and an inner cavity;

wherein the first longitudinal end of the insert comprises a flange element and the inner cavity is capable of accommodating a rod-shaped element, wherein the insert defines two spaced apart free ends at a first end of the inner cavity;

wherein the clamping element comprises an abutting surface to accommodate the flange element of the insert, and wherein the insert body inner cavity has first, second and third grooves extending longitudinally from the insert first longitudinal end to the insert second longitudinal end, the first, second and third grooves having longitudinally extending center lines offset from one another in a direction transverse to the longitudinal direction, the first, second and third grooves having different size cross-sections, the cross-sections decreasing in size inwardly from the insert cavity free ends at the cavity first end.

10. The clamping element according to claim 9, further comprising two noses to provide an abutment surface for the two free ends of the insert.

* * * * *